United States Patent [19]

Ho et al.

[11] Patent Number: 4,747,959

[45] Date of Patent: May 31, 1988

[54] ANALYTICAL METHOD AND APPARATUS FOR CHARACTERIZING LATEXES

[75] Inventors: Susanna M. Ho; Valentino G. Xanthopoulo, both of Sarnia, Canada

[73] Assignee: Polysar Limited, Sarnia, Canada

[21] Appl. No.: 37,439

[22] Filed: Apr. 13, 1987

[51] Int. Cl.$^4$ .............................................. E01D 29/00
[52] U.S. Cl. .................................... 210/768; 210/806; 210/314; 210/335; 210/348
[58] Field of Search ............... 210/767, 768, 348, 772, 210/314, 790, 323.2, 799, 335, 806, 322, 323.1, 542, 198.2

[56] References Cited

U.S. PATENT DOCUMENTS 4,366,068 12/1982 Ostreicher et al. ................. 210/767
4,529,521 7/1985 Cortes et al. .

OTHER PUBLICATIONS

Encyclopedia of Chemical Technology; Kirk–Othmer; 3rd Edition; vol. 14; p. 89.
Chemical Abstracts, vol. 104, 1986, No. 104:51408n, "Analysis of the Aqueous Phase of a Latex by Isotachophoresis".

*Primary Examiner*—Frank Sever
*Attorney, Agent, or Firm*—Stevens, Davis, Miller & Mosher

[57] ABSTRACT

Passing a sample of a liquid dispersion or emulsion of solid or immiscible liquid particles through one or more filters having a selected pore size less than 5000 A permits separation of the dispersed phase by particle size and/or separation of the dispersed phase from the continuous phase. The process is applicable to obtaining samples of dispersed particles, particularly latex, for analysis.

11 Claims, No Drawings

ANALYTICAL METHOD AND APPARATUS FOR CHARACTERIZING LATEXES

BACKGROUND OF THE INVENTION

The present invention relates to a method for directly obtaining a sample of the serum or continuous liquid phase, or a mixture of the continuous phase and a portion of the discontinuous phase of a dispersion of a discontinuous phase within a continuous liquid phase. More particularly the present invention relates to a relatively rapid sampling method for analysis of the continuous phase or a mixture of continuous and discontinuous phases of a liquid emulsion or dispersion.

Liquid emulsions and dispersions may be natural or synthetic. Naturally occurring emulsions and dispersions include such diverse products as milk and natural rubber latex. Synthetic emulsions and dispersions include monomeric emulsions and dispersions of polymers in a continuous liquid phase such as latex. In the production of emulsions and dispersions of polymers an analysis of the continuous phase provides a method for monitoring both the instantaneous and overall conversion to better control the process and to control polymer properties. In a finished latex the analysis of the continuous phase or select segments of the discontinuous phase provides insight into the chemicals and methods used in the polymerization.

There have been a number of proposals for the analysis of latex. Mechanically the serum may be separated from the polymer by centrifuging. Chemically the polymer particles may be absorbed onto the surface of various types of columns such as in isotachophoresis (Chemical Abstracts 104:51408n).

U.S. Pat. No. 4,529,521 issued July 16, 1985, assigned to The Dow Chemical Company discloses a hollow-fibre method for dialyzing a serum from a sample of latex then subjecting the dialyzate (the material passing through the membrane) to high pressure liquid chromatography to determine residual monomers or unincorporated oligomers in the aqueous phase. While the process is useful it has one drawback. It permits a sampling of the serum with solutes having a molecular weight up to about 9000. It does not allow one to pick out a selected segment of the higher polymeric portion of the dispersion.

In the hollow fiber dialysis process the fibers must be clean. This means either disposing of the fibers after each analysis or flushing and cleaning the fibers. The latter is a time consuming step. While the cost of hollow fibers for the dialysis method may seem trivial., one of the areas where rapid serum and/or latex analysis is required is in monitoring the progress of a polymerization. The cost of a fiber bundle for dialysis is in the order of $50.00 whereas the cost of the filters and a disposable syringe useful in the present invention is in the order of $3.00 to $5.00. If you wish to conduct, for example, three analysis over a 6 to 8 hour polymerization, the dialsyis process would add a cost of $150.00 to the resulting product whereas the present method would permit a comparable analysis at a cost of about $10.00 to $15.00.

The separation of various particle sizes of polymer according to the present invention gives a suggestion of the methods used to make the dispersion. This is helpful from the point of view of "reverse" engineering a latex. The same techniques are extremely useful in following the progress of a polymerization and controlling the process and the polymer properties. The present invention is directed to the analysis of dispersions or emulsion. It is known to separate bulk admixtures such as oil in water, by filtration using a No. 41 or 42 filter paper.

SUMMARY OF THE INVENTION

The present invention provides a process for directly obtaining a sample of the continuous phase, the continuous phase containing a selected portion of the discontinuous phase or the discontinuous phase of a dispersion or emulsion containing as a discontinuous phase solid or immiscible liquid particles with a particle size distribution so that at least a portion of the particles have a size less than 5000 A which comprises:
  (a) contacting said dispersion or emulsion with a conduit means;
  (b) providing a pressure differential across said dispersion or emulsion and said conduit means;
  (c) providing in association with said conduit means at least one filter means having a predetermined pore size less than 5000 A and a sample retention means associated with each filter means.

The present invention also provides in an apparatus for sampling the continuous phase, the continuous phase and a selected portion of the discontinuous phase, or the discontinuous phase of an emulsion or dispersion of solid or immiscible liquid particles having a particle size distribution so at least a portion of the particles have a size less than 5000 A the improvement characterized in that said apparatus includes:
  (1) conduit means for contacting said emulsion or dispersion.,
  (2) means for generating a pressure differential across said dispersion or emulsion and said conduit means; and:
  (3) one or more filter means having a pre-determined pore size less than 5000 A and associated sample retention means intermediate said conduit means and said means for generating a pressure differential.

The present invention also provides a process for separating the serum from an oil in water emulsion comprising subjecting said emulsion to pressure while exposing at least one surface of said emulsion to a filter means having a pore size of less than 5000A..

DETAILED DESCRIPTION OF THE INVENTION

Preferably the resulting sample of the continuous phase, or the continuous phase and a selected portion of the discontinuous phase, is subjected to one or more analytical methods selected from the group consisting of high pressure liquid chromatography, gas chromatography, mass spectroscopy, infrared spectroscopy, ultraviolet spectroscopy, Raman spectroscopy, nuclear magnetic resonance, atomic absorption spectroscopy, acid titration, base titration, conductometric titration, and electron microscopy. Other methods may be used to analyse the resulting sample. These methods will be apparent to those skilled in the analytical field.

There are many types of solid or liquid in liquid emulsions or dispersions which may be sampled in accordance with the present invention. Most commonly the emulsion or dispersion may be an emulsion of monomers in water, an oil in water emulsion, a dispersion of polymers in water or a partially polymerized emulsion of monomers in water. Liquid in liquid emulsions may be sampled in accordance with the present invention provided the dispersed phase is immisible with the continuous phase. Preferably the dispersed phase in a liquid in liquid emulsion is relatively more viscous than the continuous phase.

The basic principles of the sampling process apply to microanalysis of small samples of liquid emulsions or dispersions, or to bulk analysis of a reactor.

For micro-analysis the equipment may be as simple as a disposable hypodermic syringe. The filter means is a suitable pore sized filter such as those sold under the trademark Millipore. The pressure differential is provided by pushing or pulling the plunger in or out of the syringe cylinder and passing the samples through the filter. Drawing the sample into the syringe under pressure is less preferable than expelling it. Due to the low mechanical strength of the filters they may break when used to draw samples into the syringe. The problem may be reduced by diluting the sample to about 10 times its volume with distilled water. In the preferred expelling embodiment a sample of latex may be diluted with about four times its volume with distilled water then placed in the cylinder then expelled through the filter. One advantage of these methods is that a relatively small amount of emulsion or dispersion, in the order of 10 cc, is used.

For continuous monitoring of a sample from a reactor the conduit means may comprise a sample pipe with one or more filters and associated sample collectors. The pressure differential may be provided up stream of the filters for example by the excess pressure within the reactor relative to the atmospheric pressure. The series of filters should be arranged in order of descending pore sizes, or if a series of samples are taken individually the samples should be taken from the preceeding sample using the next smaller Pore size filter.

This permits "cuts" of a dispersion to follow particle size and monomer incorporation within a particular particle size distribution. While there are many pore sizes available the most suitable pore sizes are those which permit the passage of particles up to the following sizes: 5000 A, 3000 A, 2500 A, 2200 A, 2000 A, 1500 A, 1000 A, 500 A and 250 A. A particularly useful group of pore sizes for this type of analysis are 2000 A, 1000 A, 500 A, and 250 A. For continuous on line operation the sample line should be equipped with valves to vent the line and draw sample from a reactor; a valve to close the sample line to the reactor and open it to the atmosphere. Optionally the sample retention means could be directly connected to one more analysis means.

The process is useful with a number of types of emulsions or dispersions. The process may be used with emulsions of polymers such as styrene-butadiene polymers, acrylate polymers, ethylene vinyl acetate polymers, poly vinyl chloride polymers, and poly vinylidene chloride polymers, all of which optionally may contain up to 10 percent of one or more monomers selected from the group consisting of copolymerizable acids, amides of copolymerizable acids which may be substituted at the nitrogen atom by up to two radicals selected from the group consisting of $C_{1-4}$ alkyl and $C_{1-4}$ hydroxy alkyl radicals and copolymerizable amides.

The following examples are intended to illustrate the invention and not to limit it. In the examples parts are by dry weight unless otherwise specified.

EXAMPLE 1

A series of samples of POLYSAR Latex 793 which is a carboxylated SBR was analysed for monomeric acid in the serum phase. A sample of latex was diluted to four times its volume with deionized water.

Two samples of serum were drawn into a syringe fitted with a Swinnex (trademark) holder containing a Millipore No. VCWP 02500 microfilter. The serum was clear and was injected directly into a high pressure liquid chromatograph (HPLC) using a Biorad Aminex Ion Exclusion HPX-87H Catalog No. 125-0140 column. The analysed monomeric acid concentration by this method was 0.0256 and 0.0258 weight percent. The time for each analysis, including HPLC analysis was 30 minutes to one hour.

Three samples of POLYSAR Latex 793 were diluted to four times their volume with deionized water. The samples were analysed in accordance with applicant's understanding of the disclosure of U.S. Pat. No. 4,529,521 issued July 16, 1985 to The Dow Chemical Co. For each sample the time to clean the hollow fibers and allow them to come to equilibrium and to analyse the serum by HPLC was about 2 hours. The results of the monomeric acid analysis in these samples were 0.0218; 0.0255; 0.0247 weight percent. This example shows reasonable consistency between the method of the present invention and that of U.S. Pat. No. 4,529,521.

EXAMPLE 2

A bimodal latex having a large particle size of 2000–2300 A and a small particle size of less than 1000 A was analysed using the method of the present invention. The smaller latex particles were successfully separated from the bigger ones by the present invention. The smaller particles were then analysed by infrared spectroscopy and electron microscopy. This experiment demonstrates that the present invention permits the separation of a solid discontinuous phase of a specific size in a latex from the bulk latex.

EXAMPLE 3

A sample of crude oil obtained from Polysar Limited Corunna site was emulsified using the following procedure. 1.07 g of NaOH and 8.3 g of Pamak 25A (trade mark for an emulsifier) were added to 37.56 g of distilled water heated to 65° C. The mixture was stirred for 20 minutes then 100 g of crude oil heated to 50° C. was added to the aqueous system. The mixture was agitated for another 5 minutes and 253.1 g of distilled water was added to the mixture. The mixture was agitated for a further 10 minutes. The resulting emulsion was stable with only slight separation on standing 4 hours. On shaking, the separated phase was taken back into the emulsion. The emulsion was sampled with a syringe and a 4500 A Millipore (TM) micofilter and a 1000 A Millipore microfilter. The filtrate was then analysed. In the sample taken with the 4500 A pore size, a trace of oil in addition to the PAMAK was indicated by infrared analysis. In the sample taken with the 1000 A pore size, in the serum only PAMAK 25 A was detected. This demonstrates that it is possible to separate the serum in water emulsions using micofiltration or ultra filtration techniques. This may be useful for analysis or commercially. The remaining reserves of crude oil in Canada, United States and Venesuela are heavy crudes which are very viscous and difficult to pump in a pipeline. It has been proposed to pump these oils as aqueous dispersons. (T.H. Plegue, S.G. Frank, D.H. Fruman, and J.D. Zakin, J. Colloid and Interface Science, 114, pp 88-105, 1986). The present invention provides a method for analysis and/or separating the aqueous phase from the oil-in-water emulsion.

What is claimed is:

1. A process comprising: enabling the selection of one or more segments from an aqueous emulsion or dispersion containing as a discontinuous phase one or more members selected from the group consisting of immiscible liquids and a polymer having a molecular weight greater than 9000, said segment comprising both the continuous phase and a portion of the discontinuous phase having a particle size distribution less than 2500 Å by, passing a sample of said emulsion or dispersion through one or a plurality of filters having a pore size 2500 Å or less and retaining the filtrate segment or segments with the desired particle size distribution.

2. A process according to claim 1 wherein said emulsion or dispersion is a crude oil in water emulsion.

3. A process according to claim 1 wherein said emulsion or dispersion contains one or more dispersed liquid phases selected from the group consisting of polymers and one or more monomers.

4. A process according to claim 3 wherein said continuous or discontinuous phase is fluid and is subjected to one or more analysis selected from the group consisting of: high pressure liquid chromatography, gas chromatography, mass spectroscopy, infrared spectroscopy, ultraviolet spectroscopy, Raman spectroscopy, nuclear magnetic resonance, atomic absorption spectroscopy, acid titration, base titration, conductometric titration, and electron microscopy.

5. A process according to claim 3 wherein said discontinuous phase is solid and is subjected to one or more analysis selected from the group consisting of: gas chromatrography, mass spectroscopy, infrared spectroscopy, ultraviolet spectroscopy, Raman spectroscopy, nuclear magnetic resonance, atomic absorption spectroscopy, acid titration, base titration, conductometric titration, and electron microscopy.

6. A process according to claim 3 wherein said filter means has a pore size less than or equal to 2000 A.

7. A process according to claim 3 wherein said filter means has a pore size less than or equal to 1000 A.

8. A process according to claim 3 wherein said filter means has a pore size less than or equal to 500 A.

9. A process according to claim 3 wherein said filter means has a pore size less than or equal to 250 A.

10. In an on-line process to monitor an emulsion polymerization wherein a sample is periodically drawn from a reactor using a feed line the improvement characterized in using a sampling process according to claim 3.

11. A process according to claim 10 further including passing said sample directly to one or more analytical means.

* * * * *